US008147397B1

(12) United States Patent  
Witzmann et al.

(10) Patent No.: US 8,147,397 B1  
(45) Date of Patent: Apr. 3, 2012

(54) URETHRAL NEEDLE GUIDE DEVICE

(75) Inventors: Michael M. Witzmann, Minneapolis, MN (US); James D. Brazil, Braham, MN (US); Dean A. Klein, North Oaks, MN (US); Thomas M. Jaeger, Minnetonka, MN (US)

(73) Assignee: Carbon Medical Technologies, Inc., St. Paul, MN (US)

( * ) Notice: Subject to any disclaimer, the term of this patent is extended or adjusted under 35 U.S.C. 154(b) by 1129 days.

(21) Appl. No.: 11/565,950

(22) Filed: Dec. 1, 2006

Related U.S. Application Data

(60) Provisional application No. 60/747,759, filed on May 19, 2006.

(51) Int. Cl.  
*A61M 31/00* (2006.01)

(52) U.S. Cl. .......................................... 600/29; 604/48

(58) Field of Classification Search .............. 600/29–30, 600/37, 135; 606/147, 150; 227/175.1, 176.1, 227/179.1  
See application file for complete search history.

(56) References Cited

U.S. PATENT DOCUMENTS

| | | | | |
|---|---|---|---|---|
| 3,841,304 | A | * | 10/1974 | Jones .............................. 600/29 |
| 4,950,267 | A | | 8/1990 | Ishihara et al. |
| 5,258,028 | A | | 11/1993 | Ersek et al. |
| 5,336,263 | A | | 8/1994 | Ersek et al. |
| 5,409,453 | A | * | 4/1995 | Lundquist et al. .............. 604/22 |
| 5,451,406 | A | | 9/1995 | Lawin et al. |
| 5,454,782 | A | | 10/1995 | Perkins |
| 5,465,894 | A | * | 11/1995 | Clark et al. ................. 227/175.1 |
| 5,562,652 | A | | 10/1996 | Davis |
| 5,588,960 | A | | 12/1996 | Edwards et al. |
| 5,591,172 | A | | 1/1997 | Bachmann et al. |

(Continued)

FOREIGN PATENT DOCUMENTS

EP 0 967 932 A1 1/2000

(Continued)

OTHER PUBLICATIONS

Q-MED AB Uro Gynecology, ZUIDEX; 6 pages, at least as early as Dec. 2001; (English Translation included).

(Continued)

*Primary Examiner* — Charles A Marmor, II  
*Assistant Examiner* — Catherine E Burk  
(74) *Attorney, Agent, or Firm* — Moore & Hansen, PLLC

(57) ABSTRACT

Methods and devices for treating female urinary incontinence by injecting bulking material into the female urethral wall. Some devices include a handle, an elongate member attached to the handle, and a vacuum generating syringe removably secured to the handle. The elongate member can include a distal portion projecting distally from the handle, the distal portion having a wide proximal region, a narrowing shoulder, and a narrow distal region. The elongate member can include one or more vacuum ports on either side of the shoulder region. The shoulder can include a distally facing needle aperture allowing passage of a needle for injecting bulking agent. A rotatable connection between the elongate member and the handle facilitates rotatable positioning of the elongate member to permit injection of bulking material at different locations around the urethral wall. In use, the urethral tissue can be pulled to conform against the device elongate member by generating a vacuum through the elongate member ports, inserting the needle through the elongate member and needle aperture, and predictably injecting bulking material inside of and along the immobilized urethral wall. The self contained vacuum generator, simple design and wide allowable margin of needle travel allow for use in a practitioner's office.

14 Claims, 14 Drawing Sheets

U.S. PATENT DOCUMENTS

| | | | |
|---|---|---|---|
| 5,776,124 A * | 7/1998 | Wald | 604/403 |
| 5,827,216 A * | 10/1998 | Igo et al. | 604/21 |
| 5,947,929 A * | 9/1999 | Trull | 604/152 |
| 6,071,230 A | 6/2000 | Henalla | |
| 6,277,392 B1 | 8/2001 | Klein | |
| 6,325,798 B1 | 12/2001 | Edwards et al. | |
| 6,338,345 B1 * | 1/2002 | Johnson et al. | 128/897 |
| 6,358,197 B1 * | 3/2002 | Silverman et al. | 600/29 |
| 6,432,045 B2 | 8/2002 | Lemperle et al. | |
| 6,460,219 B2 | 10/2002 | Domenig et al. | |
| 6,461,332 B1 * | 10/2002 | Mosel et al. | 604/174 |
| 6,470,219 B1 | 10/2002 | Edwards et al. | |
| 6,572,532 B1 | 6/2003 | Pratt et al. | |
| 6,666,848 B2 | 12/2003 | Stone | |
| 6,695,764 B2 | 2/2004 | Silverman et al. | |
| 6,725,866 B2 | 4/2004 | Johnson et al. | |
| 6,860,516 B2 | 3/2005 | Ouchi et al. | |
| 2003/0036804 A1 | 2/2003 | Thomas et al. | |
| 2003/0161824 A1 | 8/2003 | Rackley et al. | |
| 2003/0181897 A1 | 9/2003 | Thomas et al. | |
| 2003/0208209 A1 * | 11/2003 | Gambale et al. | 606/144 |
| 2004/0138531 A1 * | 7/2004 | Bonner et al. | 600/156 |
| 2004/0215179 A1 * | 10/2004 | Swoyer et al. | 606/32 |
| 2004/0249239 A1 | 12/2004 | Silverman et al. | |
| 2005/0049459 A1 | 3/2005 | Hern | |
| 2005/0085695 A1 | 4/2005 | Shener et al. | |
| 2005/0096497 A1 | 5/2005 | Gerber et al. | |
| 2005/0096751 A1 * | 5/2005 | Gerber et al. | 623/23.66 |
| 2005/0192543 A1 | 9/2005 | Sibbitt | |
| 2006/0094929 A1 * | 5/2006 | Tronnes | 600/104 |

FOREIGN PATENT DOCUMENTS

| | | |
|---|---|---|
| GB | 2 284 158 A | 5/1995 |
| JP | 2 121675 A | 5/1990 |
| WO | WO 92/10142 A1 | 6/1992 |
| WO | WO 96/16606 A1 | 6/1996 |
| WO | WO 96/35464 A1 | 11/1996 |
| WO | WO 98/22040 A1 | 5/1998 |
| WO | WO 99/47069 A1 | 9/1999 |
| WO | WO 02/15796 A2 | 2/2002 |
| WO | WO 2004/010843 A2 | 2/2004 |
| WO | WO 2004/112596 A1 | 12/2004 |

OTHER PUBLICATIONS

J. Tamanini et al., Macroplastique Implantation System for the Treatment of Female Stress Urinary Incontinence; The Journal of Urology; Jun. 2003; vol. 169; pp. 2229-2233.

ZUIDEX System, A four-point advantage for SUI, Instruction guide; pp. 1-34; Sep. 2006. (English Translation included).

* cited by examiner

URETHRAL NEEDLE GUIDE DEVICE

RELATED APPLICATIONS

The present application is a non-provisional of U.S. Provisional patent Application No. 60/747,759, filed May 19, 2006, titled VACUUM ASSIST URETHRAL BULKING AGENT PLACEMENT DEVICE, herein incorporated by reference in its entirety.

FIELD OF INVENTION

The present invention is related generally to medical devices for treating incontinence through injection of a bulking agent. More specifically, the present invention is related to devices and methods for injecting bulking agent within the urethral wall to treat female urinary incontinence.

BACKGROUND

There are several approaches for treating female urinary incontinence. One approach involves the submucosal injection of a biocompatible bulking agent into tissue sites adjacent the urethral canal, and/or the bladder neck in order to modify the shape of the tissue sites and/or to provide for improved closure or occlusion between the urethra and the bladder. One particularly suitable bulking agent for this application is sold under the brand name Durasphere® EXP, and is manufactured by Carbon Medical Technologies, St. Paul Minn.

U.S. Pat. Nos. 6,277,392 (Klein et al.) and 5,451,406 (Lawin et al.), both herein incorporated by reference, describe how bulking agent may be submucosally injected using a suitably sized and shaped needle, which is connected to a syringe containing the bulking agent. The needle may be inserted into the patient either outside of and adjacent to, or directly into, the urethra. The tip of the needle may then be positioned in a submucosal tissue site adjacent the urethral canal and/or bladder neck. The bulking agent may then be injected into the submucosal tissue site. The process is normally repeated several times around the circumference of the urethra. An endoscope may be used to view the patient's urethra during the process.

Clinicians face several challenges in performing this process. One challenge is determining the proper placement of an injection guide device and hence the injection needle. Some injection guide devices require visualization and possible trial and error in order to properly set the depth of the guide device, so as to accurately locate the injection target along the urethral wall. Another challenge is injecting the bulking agent at the correct depth into the urethral wall. If the bulking agent is injected too close to the surface, the bulking agent may rupture through the urethra tissue and into the canal. If the bulking agent is injected too far beneath the surface, the bulking agent may be ineffective. Some devices require rather specialized support accessories, such as a ready source of vacuum or visualization equipment, which may be common in some medical specialists' offices, but may not be available to all practitioners.

What would be desirable is a device for injecting bulking agent that can reliably and repeatedly inject the bulking agent at the proper location, with little need for complex added equipment, and not require undue complexity in manipulating the device.

SUMMARY

The present invention provides a method for augmenting tissue within a urethral wall of a urethra. One method includes displacing a first portion of the urethral wall by applying suction to the urethral wall to form an immobilized transition wall region conforming to a suction applying device, followed by advancing a needle having a lumen therethrough to contact the transition wall region.

The method can also include inserting the needle into the urethral wall at the transition wall region along a path that is substantially parallel to the urethral wall distal of the transition region. The suction force application may then be stopped. A bulking agent can then be injected through the needle lumen and into the urethral wall.

In some such methods, the needle travels a first distance during the inserting, in which the injecting is performed at a second distance beneath the urethral wall, wherein the first distance is at least about twice or three times the second distance. That is, the needle can travel a path at least about twice or three times the distance that the needle lies beneath the urethral wall, as the needle may then be traveling parallel to the immobilized urethral wall.

The present invention can also provide another method for augmenting tissue within a urethral wall, where the urethra has an interior, a center longitudinal axis, and an inner surface. The method can include applying suction to a first tissue surface region, and pulling the first tissue region in the direction of the urethral interior to form a transition urethral wall region which conforms to a shape which places the transition region in the path of a bulking agent delivery needle. A second tissue surface region lies proximal of the transition region. A needle can be advanced into the urethra, the needle further inserted into the transition region, and a bulking agent injected within the urethral wall. The inserting may be along a longitudinal axis of the urethral lumen. The injecting can be at a depth at least about two or three times the shortest distance from the needle tip to the urethral wall.

The suction can be provided by a vacuum generated within a vacuum creating device operably coupled to a vacuum lumen in a bulking agent injection tool. The vacuum creating device is preferably a vacuum generating syringe. The needle inserting may occur through a needle receiving channel disposed in an elongate body portion of the tool. The elongate body may be rotatably disposed within a handle, with the suction being supplied by a vacuum generated in a vacuum creating device operably coupled to the handle. The vacuum may be generated in a syringe operably coupled to the handle. The needle can be retracted within the rotatable body after the injection, the body rotated, and a vacuum applied to a different tissue wall location. The needle can then be inserted into the different wall region, and additional bulking agent injected.

In some devices, a rotation selection knob forms a proximal portion of the rotatable body, having clock face indicia displayed on the selector knob. Some devices have a limited number of stable positions for the selector knob, and a mechanism for urging the selector knob into one of those limited number of positions. In one such device, the number of positions is 12, evenly spaced apart from each other.

The present invention can also provide an apparatus for augmenting female urethral tissue, the apparatus including a handle and an elongate member rotatably coupled to the handle. The rotatable member can have a distal portion extending distally from the handle, the distal portion having a distal region, a proximal region, and a shoulder region therebetween. The distal portion can include at least one outwardly facing vacuum port. The distal region can have a vacuum lumen in fluid flow communication with the vacuum ports and with a vacuum source. A channel for receiving a needle can be disposed within the body, with the channel having a distal aperture disposed proximal of at least one of the vacuum ports. The distal needle aperture lies within the shoulder region in some embodiments. The elongate member distal region has a substantially uniform width over its length in most embodiments.

In some embodiments, the rotatable elongate member has a center of rotation, in which the needle receiving channel is offset from the center of rotation, such that rotating the elongate body rotates the channel about the center of rotation. The rotatable elongate member may be disposed substantially orthogonal to the handle. The device may further include a vacuum generating device operably coupled to the handle for providing a vacuum to the vacuum lumen. The vacuum generating device can include a syringe operably coupled to the handle.

These and other objects and advantages of the invention will be readily understood as the following description is read in conjunction with the accompanying drawings wherein like reference numerals have been used to designate like elements throughout the several views.

DETAILED DESCRIPTION

Figure 1:
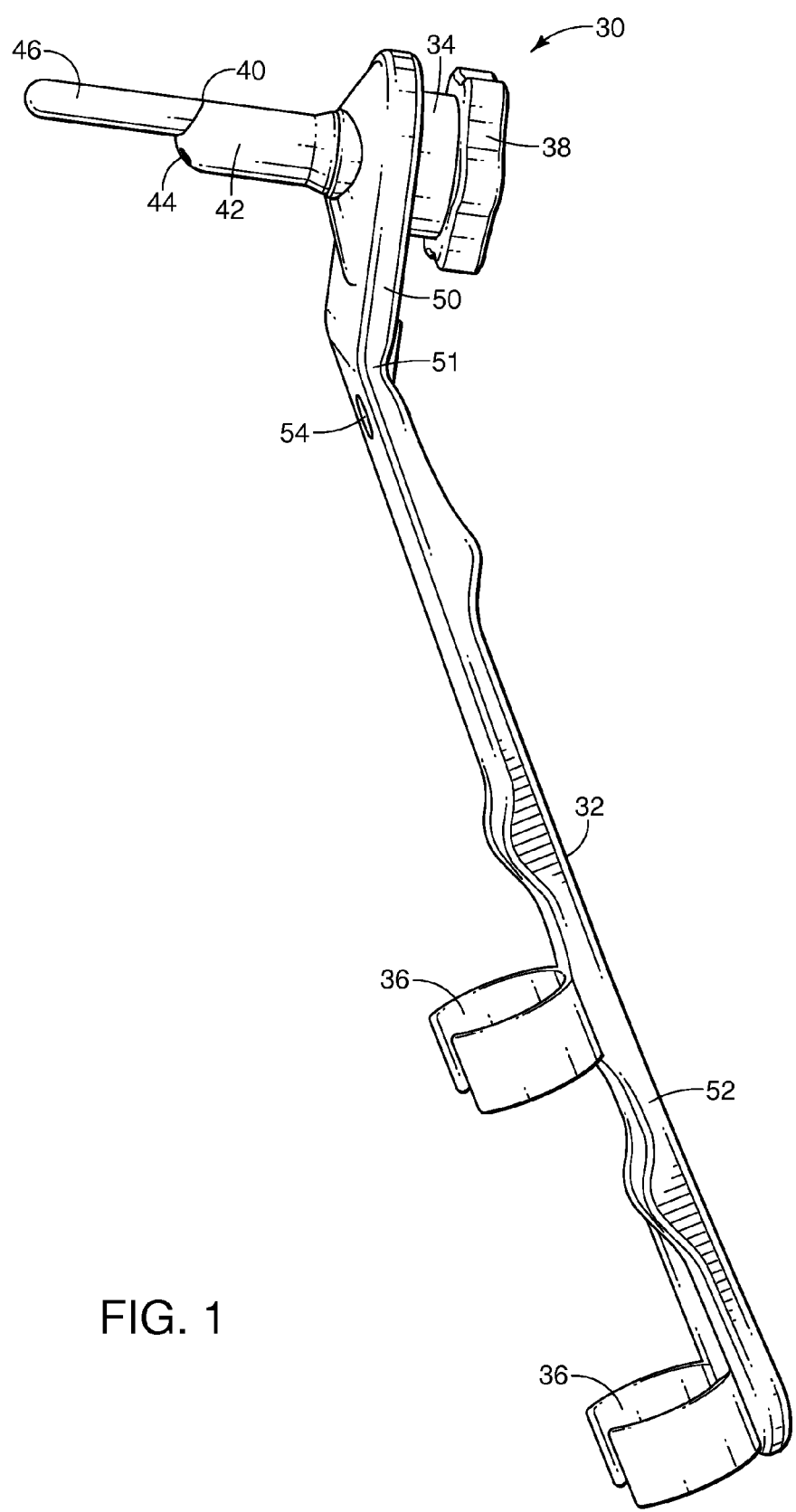
FIG. 1 is a perspective view of a urethral needle guide device having a handle, a rotatable body, and clips for receiving a vacuum producing syringe.

FIG. 1 shows a vacuum assist device 30 having generally a handle 32, a rotatable body 34, and clips or arms 36 for receiving and releasably retaining a vacuum producing syringe. Rotatable body 34 includes a proximal rotation selection knob 38 and an elongate member 40. Elongate member 40 includes a wider, proximal region 42, a shoulder or transition region 44, and a narrower distal region 46. Shoulder region 44 has an aperture therein allowing the passage of a tissue bulking needle therethrough. Handle 32 includes a handle upper portion 50, a bend 51, and a vacuum line aperture 54 therethrough. Handle 32 also includes a handle lower portion 52 on which spaced apart syringe clips 36 are provided.

Figure 2:
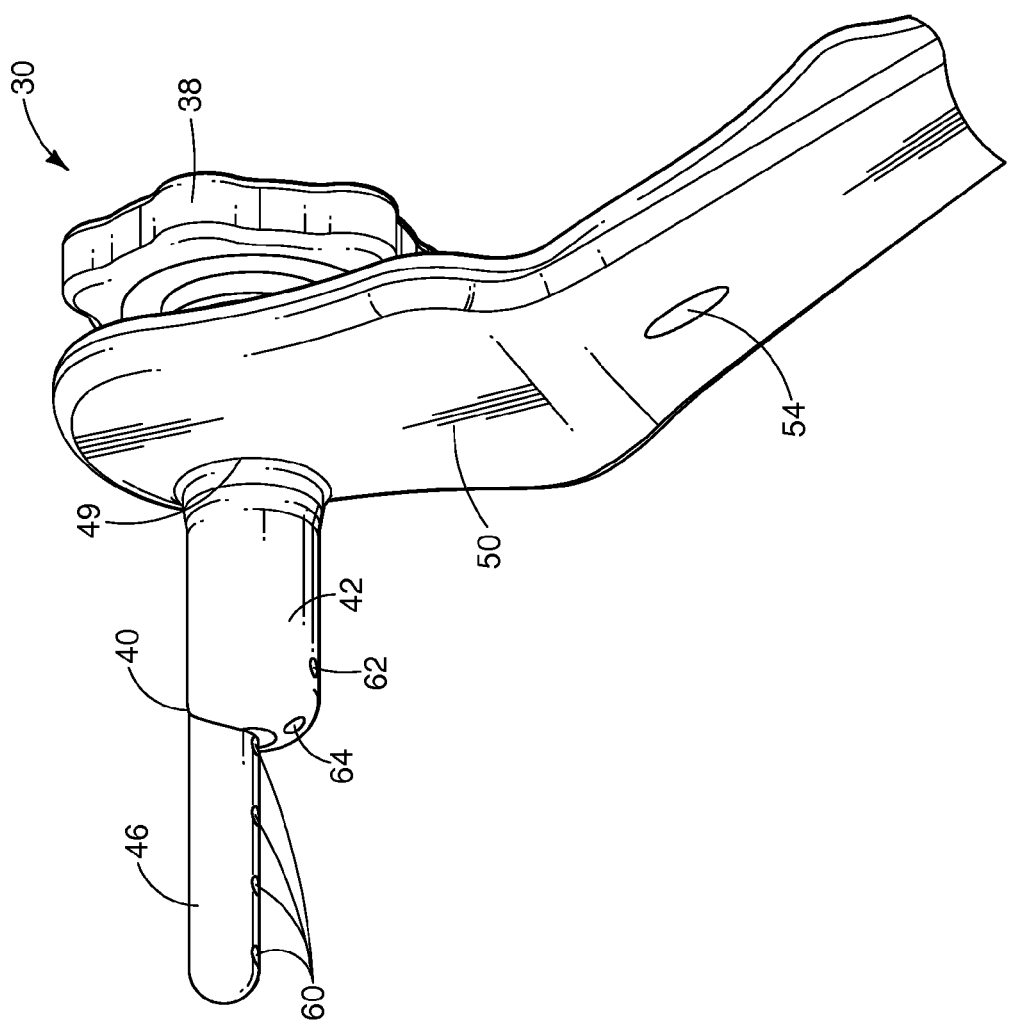
FIG. 2 is a fragmentary, bottom, perspective view of the device of FIG. 1, showing the body distal portion having the side-facing vacuum ports and the shoulder region having the distally facing needle aperture.

FIG. 2 shows device 30 in greater detail. Device 30 includes rotation selection knob 38, handle upper portion 50, and vacuum line aperture 54, as previously described. Vacuum line aperture 54 can be used for passage of a vacuum tube from the vacuum syringe on the lower end of the handle, upward to the vacuum lumen or lumens of the device elongate member 40. Elongate member 40 shows proximal region 42, transition or shoulder region 44, and distal region 46, in greater detail. Distal region 46 may be seen, in this embodiment, to be substantially uniform in width over its length and have a rounded distal tip. Distal region 46 also is shown to have, in this example of the invention, four side-facing vacuum ports 60. In this embodiment, proximal, wider region 42 also has a single side facing vacuum port 62 which can serve to immobilize tissue against elongate member 40. Transition or shoulder region 42 may be seen to have a distally projecting aperture 64 for allowing the passage of a tissue bulking needle distally therethrough. Tissue conformed to shoulder 44 will have the needle passing through it at a substantially non-parallel, that is acute, angle, in some embodiments. The shoulder and conformed tissue thus form a plane or surface which intersects a distal extension of the needle lumen, where the needle lumen is preferably substantially parallel to the center longitudinal axis of the inserted device portion. Elongate body 40 is rotatably disposed within orifice 49 of handle upper portion 50. Vacuum ports 60 can act to conform the urethral wall tissue to elongate body 40, including a transition region of tissue passing in front of needle aperture 64. Vacuum ports 60 and 62 can act to hold the tissue in place to inhibit sliding of the device relative to the tissue during treatment.

Figure 3:
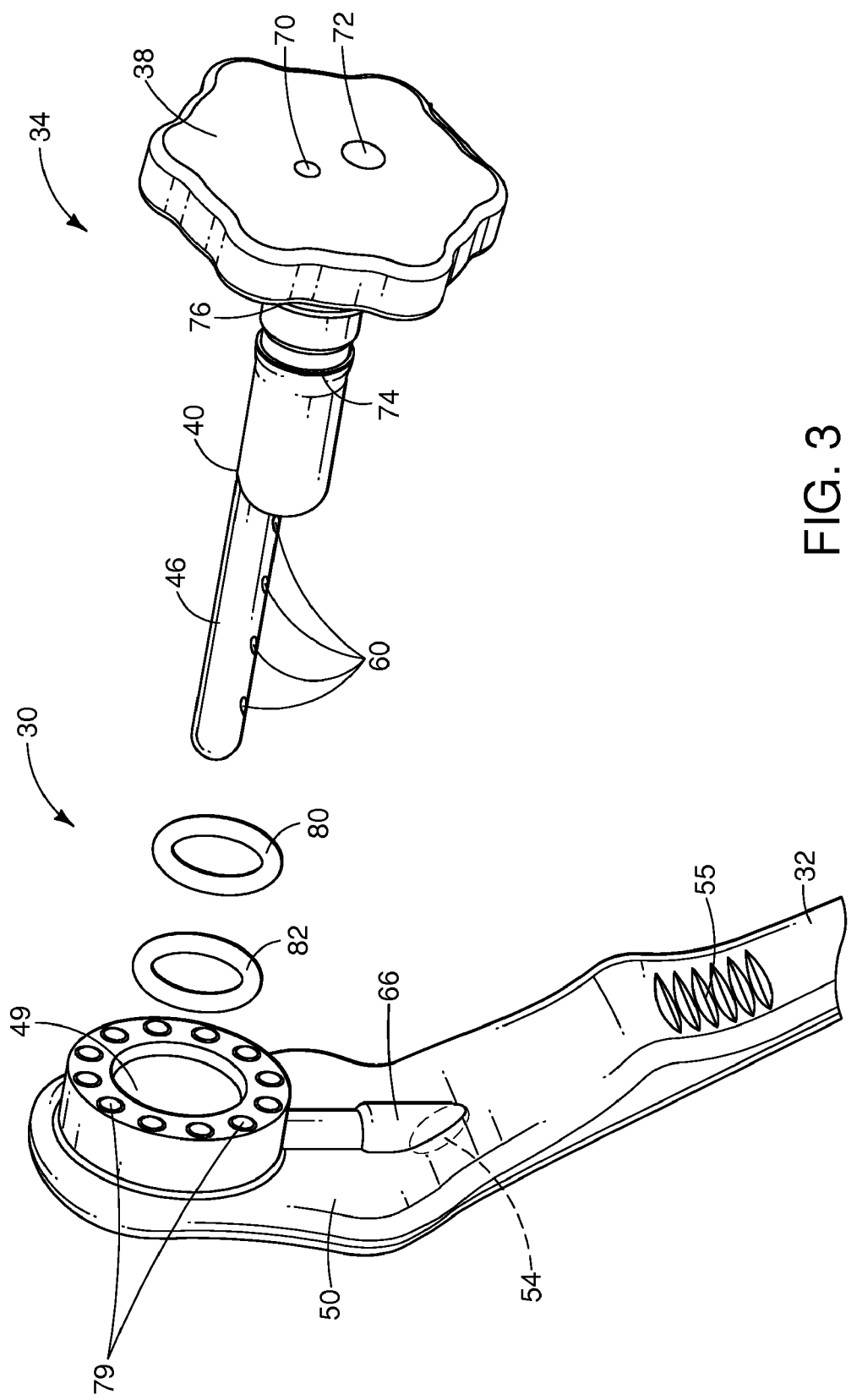
FIG. 3 is a fragmentary, exploded view of the body and handle of FIG. 1, showing sealing O-rings and the outer profile of a vacuum lumen within for providing the vacuum to the annular vacuum lumen of the body.

FIG. 3 shows an exploded view of device 30. The handle orifice 49 for receiving elongate member 40 is better seen as is a vacuum lumen outer profile 66 in communication with vacuum aperture 54, previously described. Ridges or finger grips 55 are provided on handle 32. Rotation selection knob 38 includes an optional vacuum lumen external port 70 and a needle port 72 for admitting the tissue bulking needle. Optional vacuum or visualization port 70 may be blocked or non-existent in some embodiments. In some embodiments, vacuum port 70 may have a removable plug for sealing the port. Port 70 may be used to pass a visualization device, for example, a fiber optic probe, to the end of the vacuum lumen to allow for visual inspection of the device position. In a preferred embodiment, as shown in FIG. 3, needle admission port 72 is off-center with respect to a center of rotation of elongate body 40 and needle exit aperture 64 (shown in FIG.

2). Needle admission port 72 is also preferably longitudinally in line with shoulder portion 44. Having needle port 72 off-center allows the rotation of rotation selection knob 38 to cause the port to rotate to different angular or clock positions in the urethral channel for injecting bulking material into different locations. A groove 74 on elongate body 40 allows a snap fit of the handle to rotatable body 34. An annular vacuum channel 76 serves to transmit the vacuum from the vacuum source to the vacuum ports 60 in elongate member distal portion 46. Such an annular channel allows transmission of vacuum even when the rotatable member is rotated in different clockwise positions. O-rings 80 and 82 provide a seal on either side of annular vacuum channel 76. Several bumps 79 are present on the surface of handle 32 surrounding orifice 49. Bumps 79 can be used to urge rotation selection knob 38 into one of a limited number of stable positions, discussed further below. Some embodiments may have 4 or 12 bumps evenly spaced from each other.

Figure 4:
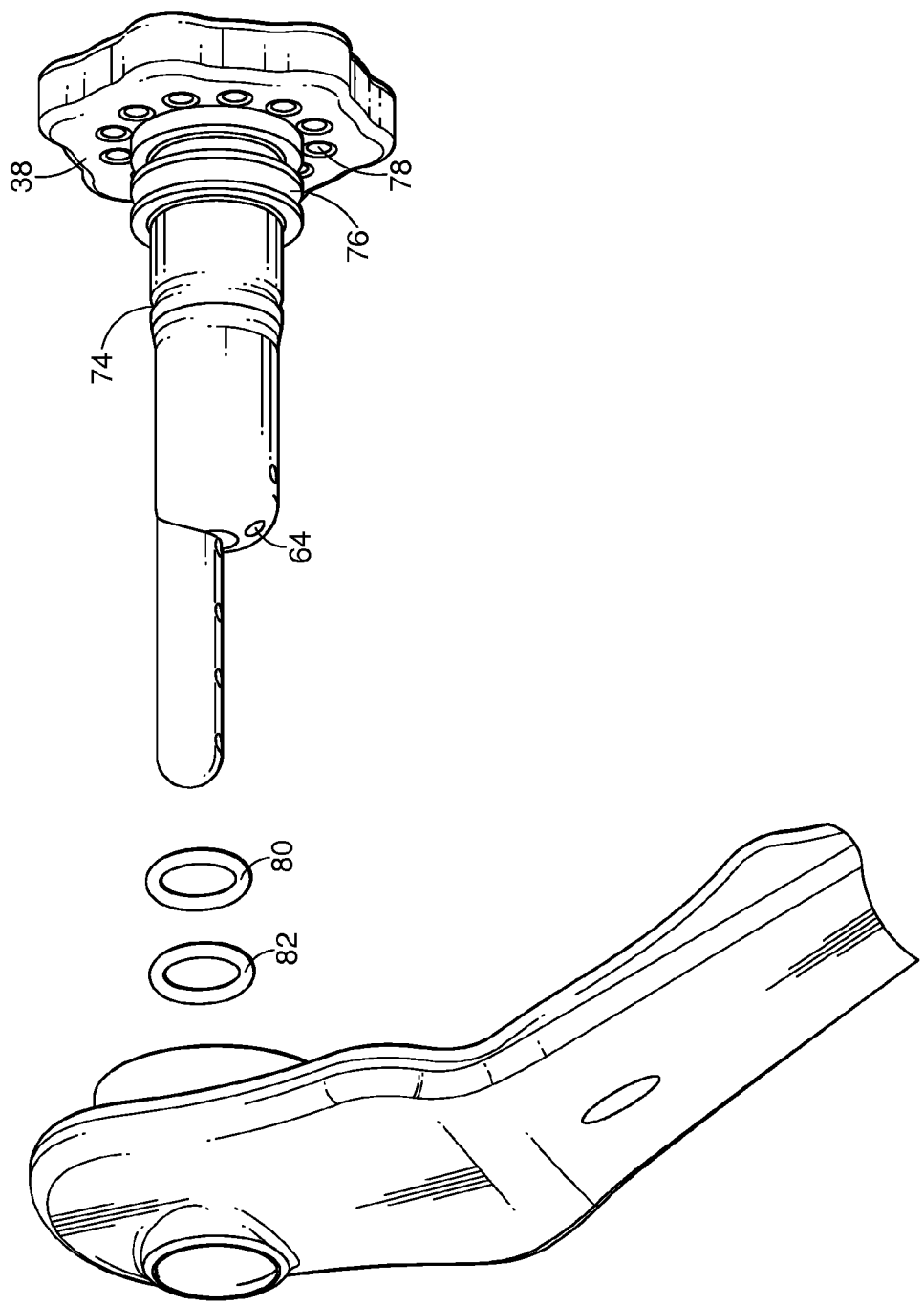
FIG. 4 is another, fragmentary, exploded view of the device of FIG. 3, showing the elongate body and the annular vacuum channel.

FIG. 4 is a view of device 30 similar to that of FIG. 3, with the distal side of rotation selection knob 38 being better shown, illustrating the dimples 78 which engage bumps 79 shown in FIG. 3. In one embodiment, there are 12 dimples spaced evenly apart from each other, in the 12 hourly clock face positions. The dimples and bumps engage each other to urge rotation selection knob 38 into one of 12 different stable positions. In some embodiments, visual indicia are provided on the proximal face of rotation selection knob 38 to indicate at which clock position the needle is positioned. O-rings 80 and 82 are disposed on either side of annular vacuum channel 76, that is, one proximal and one distal of the channel, for maintaining the vacuum.

Figure 5:
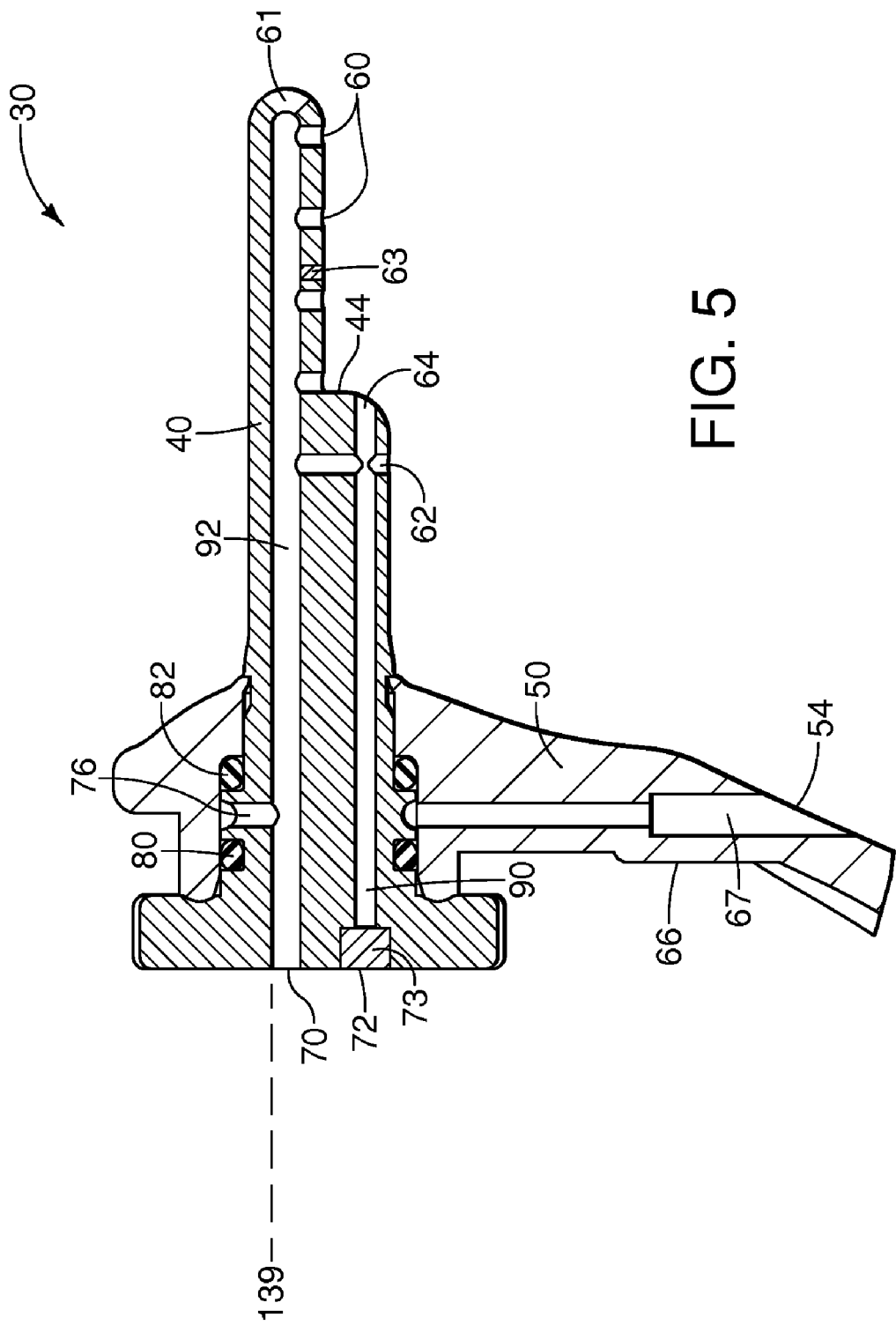
FIG. 5 is a fragmentary, cross-sectional view of the urethral needle guide device of FIG. 1, showing the vacuum lumen, the injection/needle lumen, and the O-rings for maintaining the vacuum.

FIG. 5 shows a longitudinal cross-sectional view through device 30. Optional vacuum port 70 and needle port 72 are as previously described. An elastomeric seal or septum 73 can seal needle port 72 to allow passage of the bulking agent delivery needle while maintaining the vacuum. O-rings 80 and 82 may be seen in place, providing seals on either side of annular vacuum channel 76. A vacuum lumen 92 extends between port 70 and the multiple side facing vacuum ports 60 and side facing vacuum port 62. A needle lumen 90 terminates in distal needle aperture 64, and rotates as elongate body 40 is turned, about a center of rotation 139 of elongate body 40. Vacuum ports 60 and 62 thus extend along elongate body 40, proximal of and distal of needle aperture 64. In one embodiment, as shown in FIG. 5, a rigid lumen outer profile 66 extends within handle 50, providing a vacuum passage 67 from vacuum aperture 54 to annular channel 76. The vacuum can be provided to aperture 54 from a flexible tube 212 coupled to a syringe 200 (both shown in FIG. 7).

A lens 61 may be located at the distal end of lumen 70, to allow for visualization in some embodiments. Lens 61 may be used in conjunction with an integral fiber optic device or used in conjunction with an inserted, removable fiber optic device, depending on the embodiment. In some embodiments, a small electronic viewing device may be used in place of lens 61 to visualize the urethra, bladder, and the treatment progress. In one example, a camera element is used. In another example, a CCD type camera may be used. A pressure sensor 63 is also shown, which can be coupled via a signal transmission line (not shown and not requiring separate illustration) to a more proximal portion of the device. A ring shaped sensor may be used in some embodiments and a less extensive sensor may be used in other embodiments. Pressure sensors are well known to those skilled in the art, and can include strain gauges, piezo-electric elements, and the like. The pressure sensor may be used to measure inwardly (radially) directed urethral wall pressure bearing against the elongate member 40. The pressure may be measured before, during, and after the tissue bulking procedure, in order to gauge the progress of the bulking agent injection near and around elongate member 40.

Figure 6:
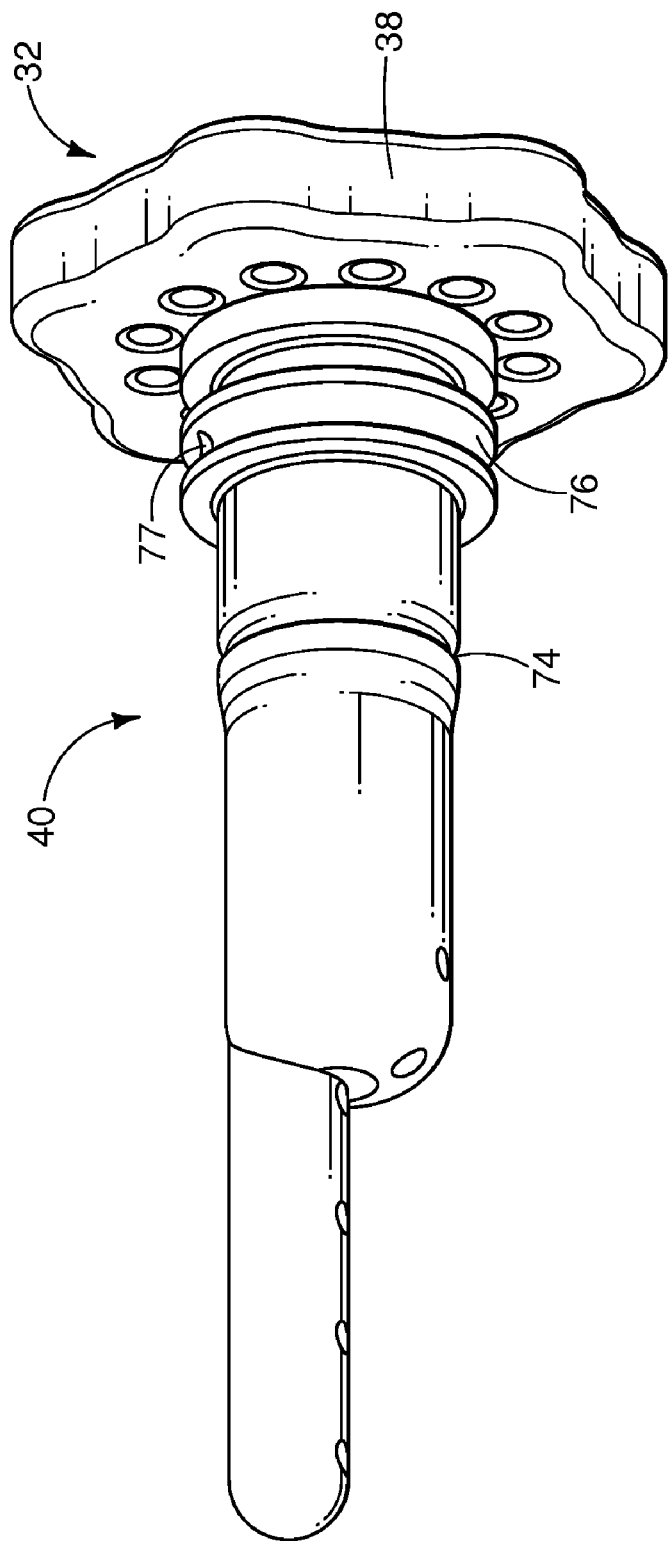
FIG. 6 is a fragmentary, perspective view of the body of FIG. 1, better illustrating the annular vacuum channel.

FIG. 6 shows device 30 and elongate member 40 in even greater detail. Rotation selection knob 38 and vacuum channel 76 are shown. A vacuum port 77 is also shown, extending into annular channel 76 for bringing the externally produced vacuum through to the annular channel, then to vacuum lumen 92 and vacuum ports 60 (shown in FIG. 5). Groove 74 may be seen, as previously described, allowing the snap fit of elongate member 40 within the handle.

Urethral needle guide device 30 may be made from a variety of materials well known to those skilled in the art. The rigid portions, including the handle and rotatable body, may be made from polyethylene, PTFE, Polyether block amide (available from Arkema under the brand name PEBAX®), Delrin® polymer (available from DuPont) and/or mixtures of various polymers. The O-rings are of conventional construction, and can be provided in various shapes to maintain the vacuum seal. Vacuum generating syringes used in the present invention may be made of various suitable polymers, for example, polycarbonate. While polymers are preferred for construction of disposable and some sterilizable devices, non-disposable devices may be made of stainless steel.

Figure 7:
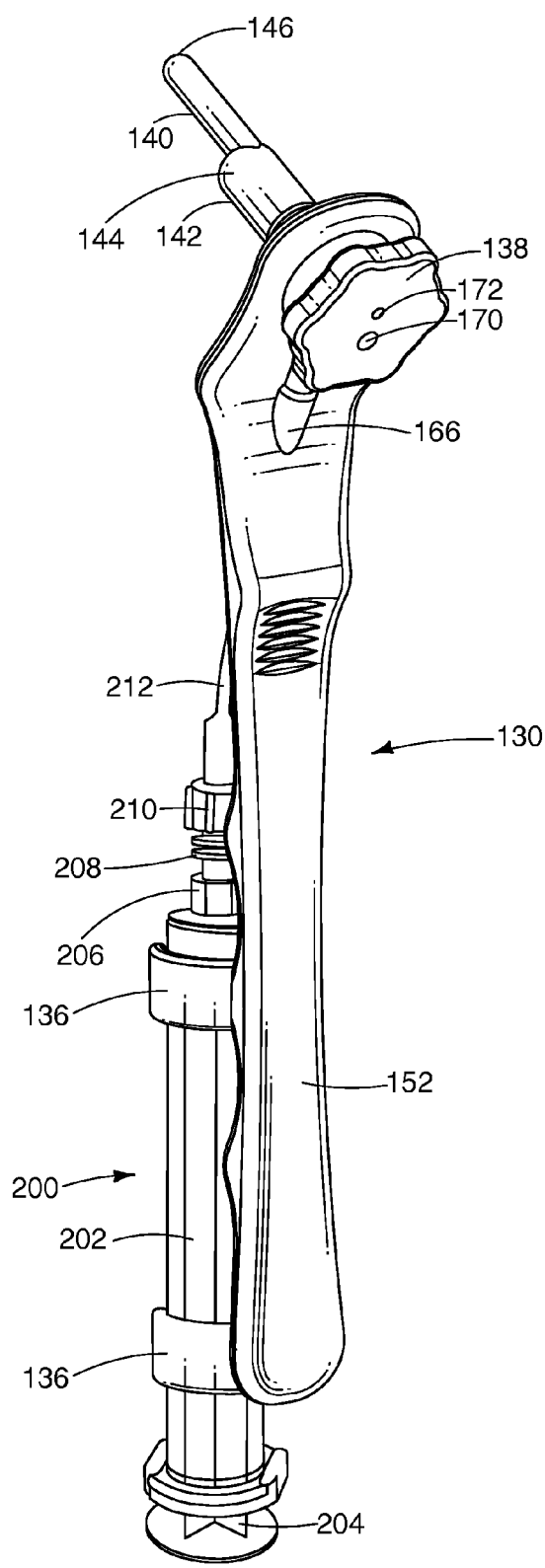
FIG. 7 is a perspective view of a prototype according to the present invention, showing the vacuum producing syringe clipped to the handle and coupled to the device vacuum tube through a Luer fitting.

FIG. 7 shows a prototype of a vacuum assist urethral needle guide device 130. Device 130 includes a handle 152, a rigid vacuum lumen outer profile 166, a rotation selection knob 138 carrying a vacuum port 170, and a needle admission or entry port 172. Rotation selection knob 138 is rotatable within an upper handle portion 150. An elongate body portion 140 may be seen having a proximal, wide region 142, a transition or shoulder region 144, and a distal region 146. Elongate body 140 can carry the vacuum ports (present, but not easily seen in FIG. 7), as previously described. Transition region 144 can carry the distally facing needle exit aperture, as described above. Needle aperture 172 is located off-center of the center of rotation of rotation selection knob 138 (and of elongate body 140), allowing different angular positions of the urethra to be injected by rotating selection knob 138 to different angular positions. Handle 152 includes clips or arms 136, as previously discussed. Clips 136 may be seen releasably holding a vacuum producing syringe 200. Syringe 200 can be of standard manufacture, and include a barrel 202, and a plunger 204. Syringe 200 also includes a locking distal portion 206, and a male Luer tip 208. Male Luer tip 208 can be received within a matching female lockable Luer fitting 210 coupled to a flexible vacuum tube 212. Vacuum tube 212 can extend through the handle aperture as previously described. The vacuum can be provided from vacuum tube 212, through a vacuum lumen in handle 152, through an annular channel, and into the interior of elongate member 144, as described above with respect to FIG. 3. Other vacuum generating devices can be coupled to the handle in other embodiments. In one such example, a battery powered vacuum pump is coupled to the handle at port 70 (shown in FIG. 3). Either the vacuum syringe or the small battery powered pump eliminates the need to tether the vacuum assisted urethral treatment device through a vacuum line to a wall source or to a large floor mounted vacuum pump.

Figure 8:
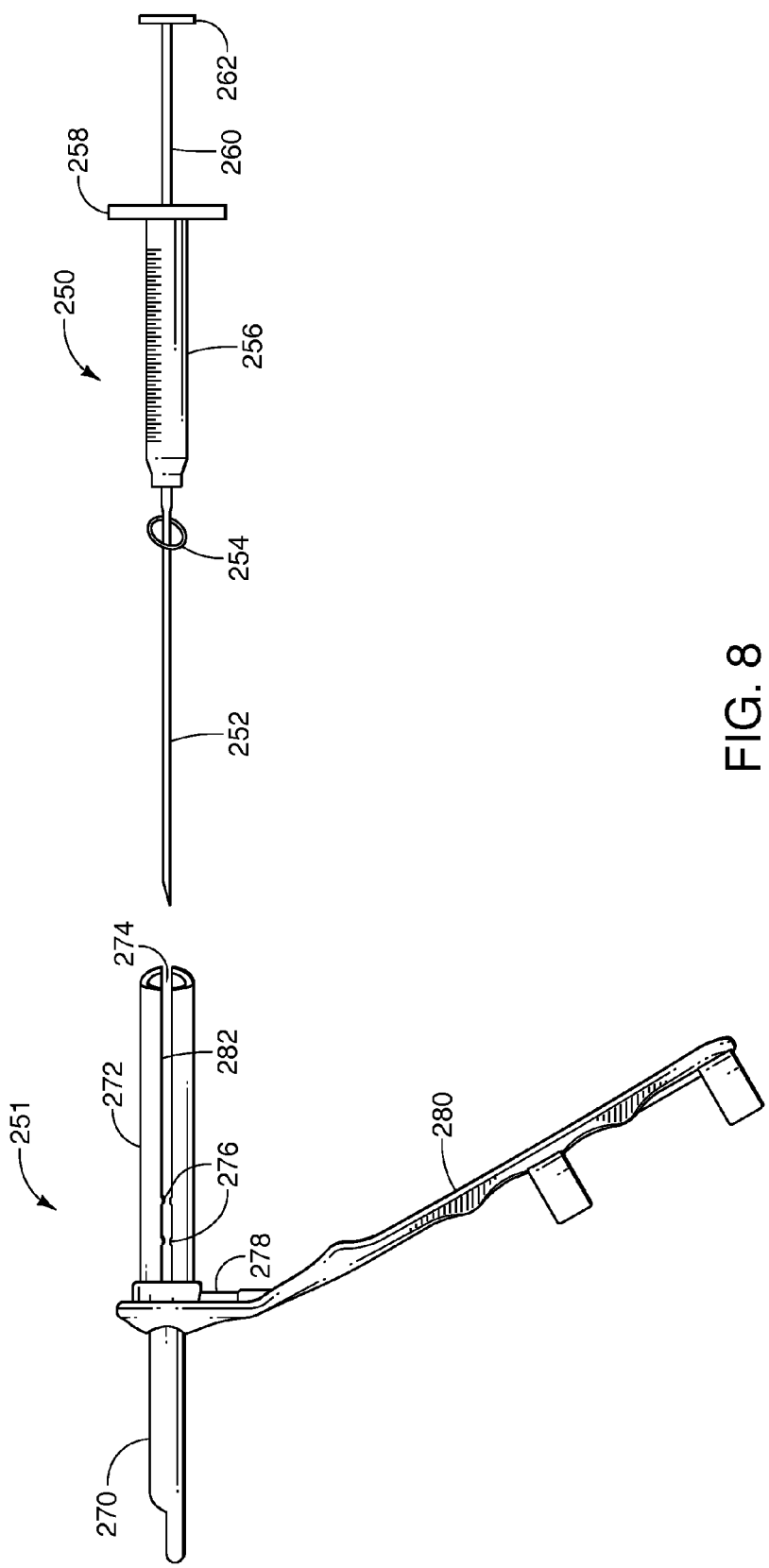
FIG. 8 is a side view of a syringe which can be used to inject bulking material through the device of FIG. 1, and another needle guiding device having a long needle lumen allowing for hands free retention of the retracted bulking agent injection syringe.

FIG. 8 illustrates a syringe 250 that can be used to inject a bulking agent into the urethra, in conjunction with the device of FIG. 1. Syringe 250 includes a hypodermic needle 252 having proximal wings 254 and coupled to a barrel 256. Barrel 256 is coupled to needle 252 using wings 254 to torque the connection. A shaft 260 is used for pushing a plunger (not visible in FIG. 8) with aid of thumb pad 262 and barrel ears 258. Any syringe capable of forcing the bulking agent down needle 252 and having a sufficiently long needle may suffice. One acceptable syringe has a capacity of about 1 ml and is about 7½ centimeters long. Some needle sizes used are of about 20 gauge. Some embodiments have a needle size of between about 18 and 25 gauge. Some embodiments have a capacity of between about 1 ml and about 3 ml. In one embodiment, the syringe has a capacity of at least about 1 ml, a needle size of at least about 20 or 22 gauge, and a needle length of at least about 6 cm and less than about 20 cm.

Another needle guiding device 251 is also illustrated, having a handle 280, a handle upper portion 278, a rotatable body including a distal portion 270 and a proximal portion 272. Proximal portion 272 can be longer than those discussed previously in the present application. Proximal portion 272 can include a pair of stops 276 within a needle lumen 282. A proximal needle admission port 274 is also shown, having a slotted shape to allow entry of wings 254. The length of needle 252 can be such that when fully inserted, it extends sufficiently far to inject bulking agent. The length of rotatable body proximal portion 272 can be such that needle 252 can be retracted from the urethral tissue and be supported within proximal portion 272. This allows the treating physician to retract the needle and remove the hand used to retract the needle, freeing the hand for other uses. The hand may then be used to rotate the rotatable body to the next 'clock' position, followed by applying vacuum, inserting the needle, releasing the vacuum, and injecting more bulking agent. In some embodiments, the needle and needle guide device are cooperatively sized and provided as a kit. In some kits, the kit is sized such that the needle, when fully advanced, does not extend substantially past the distal-most point of the guide device. Some embodiment kits are sized such that the syringe will not fall out when the needle is retracted into the guide device and the physician's hand is removed from the syringe.

Figure 9:
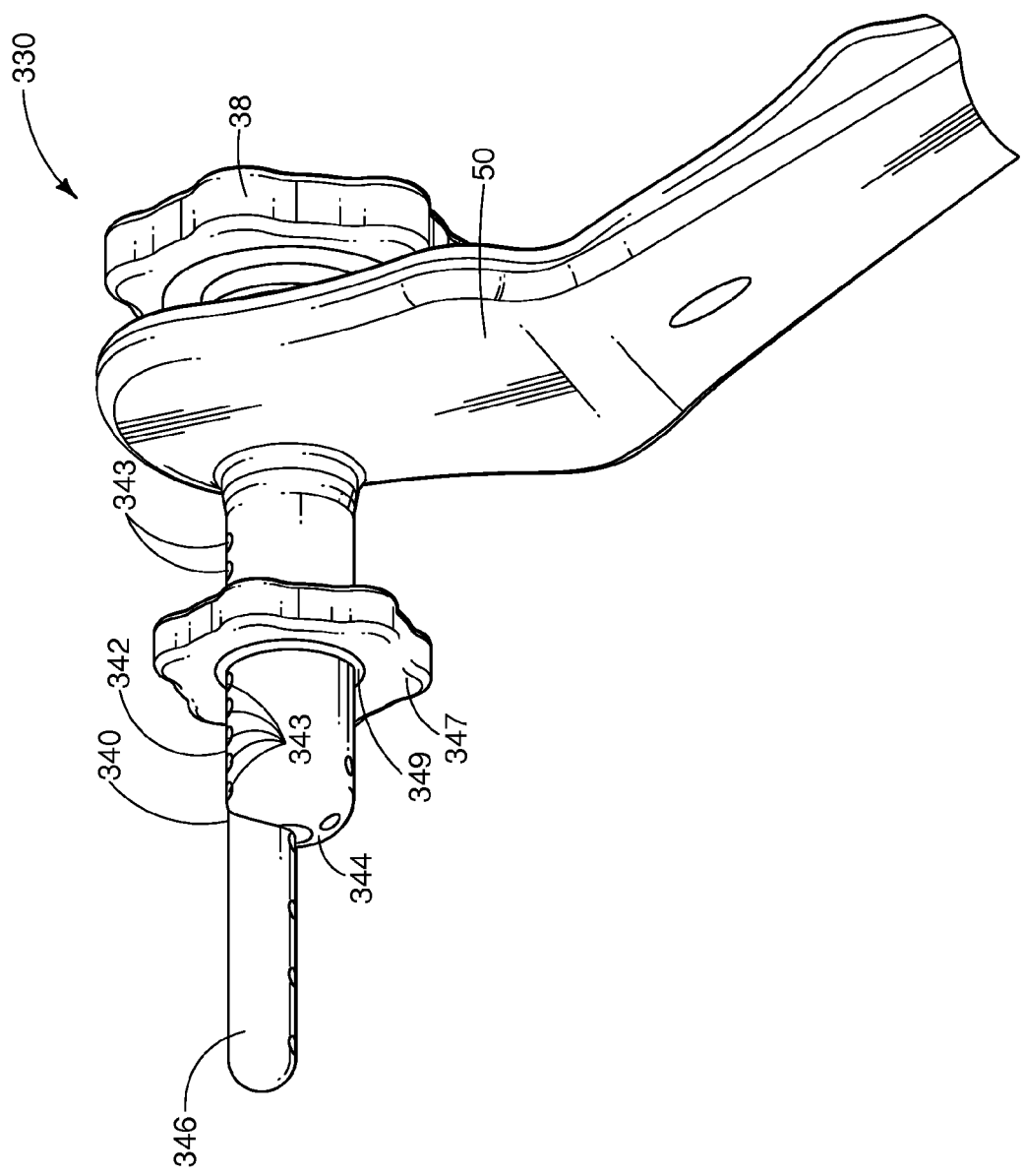
FIG. 9 is a fragmentary perspective view of another embodiment of the invention having a variable depth retainer.

FIG. 9 illustrates another embodiment of the invention having a variable depth feature. The penetration depth of the elongate member into the urethra can be varied and controlled by setting the position of a stop member along the elongate member. Device 330 includes handle 50 and rotation selection knob 38 as previously described. Device 330 also includes an elongate rotatable member 340 having a proximal portion having a distal region 346, a shoulder region 344, and a proximal region 342. Several short radial or transverse grooves 343 are formed in elongate member 340 along the top. A longitudinal groove (not visible in FIG. 9) also extends along the top and intersects grooves 343. A locking disc 347 is also provided, having an outer portion and an inner portion 349 for engaging grooves 343. Locking disc 347 serves as a stop member, limiting penetration depth into the urethra. Locking disc 347 also has a tongue or spline (not visible in FIG. 9) configured to ride in the longitudinal groove and be rotated into the appropriate groove 343 when the desired urethral penetration depth is attained. Once rotated into position, a friction fit can keep locking disc 347 in place to control the penetration depth.

Device 330 has thus been modified to allow hands-free depth control by adding locking disc 347 to elongate body 440. The elongate body 340 has been lengthened to provide greater versatility and operator space. Disc 347 could be locked in the desired position as determined by the practitioner. It would be based on urethral length and intended injection site.

The locking mechanism can be one of many designs such as a cam lock wherein the elongate body cross-section is slightly out of round and the disc has a hole to match. Under this design, the frictional fit developed when the disc assembled onto the elongate body is rotated, locks, and holds the disc in place on the elongate body.

In yet another design, a spring loaded pawl (arm) could be attached to the proximal side of the disc. The elongate body would have teeth or indexing groove(s) spaced along its length adjacent the pawl and conforming to its stop member. When the pawl is activated or lifted, the disc can be moved (slid) to a new position, released into an adjacent tooth or groove and thus locked into a new position.

Embodiments having the adjustable penetration depth can allow the practitioner to establish and set the injection distance into the urethra and maintain it while performing the procedure.

Figure 10:
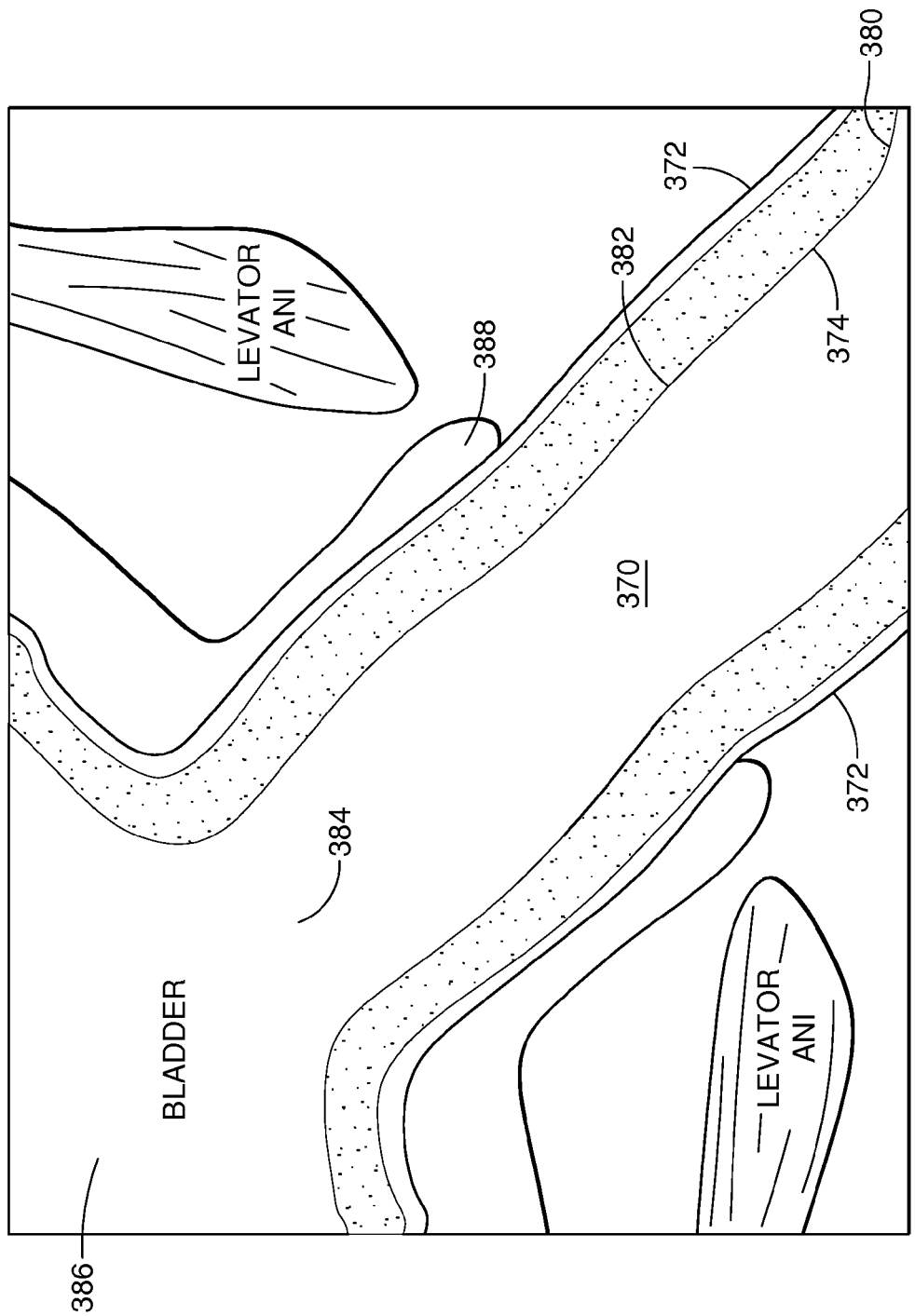
FIG. 10 is a fragmentary cross-sectional view of a female urethra.

FIG. 10 illustrates a urethra 370 having an inner mucosal wall 374, a submucosal layer 372, and an external sphincter 388. Urethra 370 extends from a far proximal region 380, through an intermediate region 382, and terminates in a far distal region 384 in a bladder 386. As used herein, unless specified otherwise, the terms "proximal region", "intermediate region", and distal region" are used relative to each other to describe relative urethral wall locations. As used herein, unless specified otherwise, the terms "proximal region", "intermediate region", and distal region" are not used to limit these locations to the far proximal region, the urethral region in the exact middle between the far proximal and far distal regions, or the far distal region, respectively.

Figure 11:
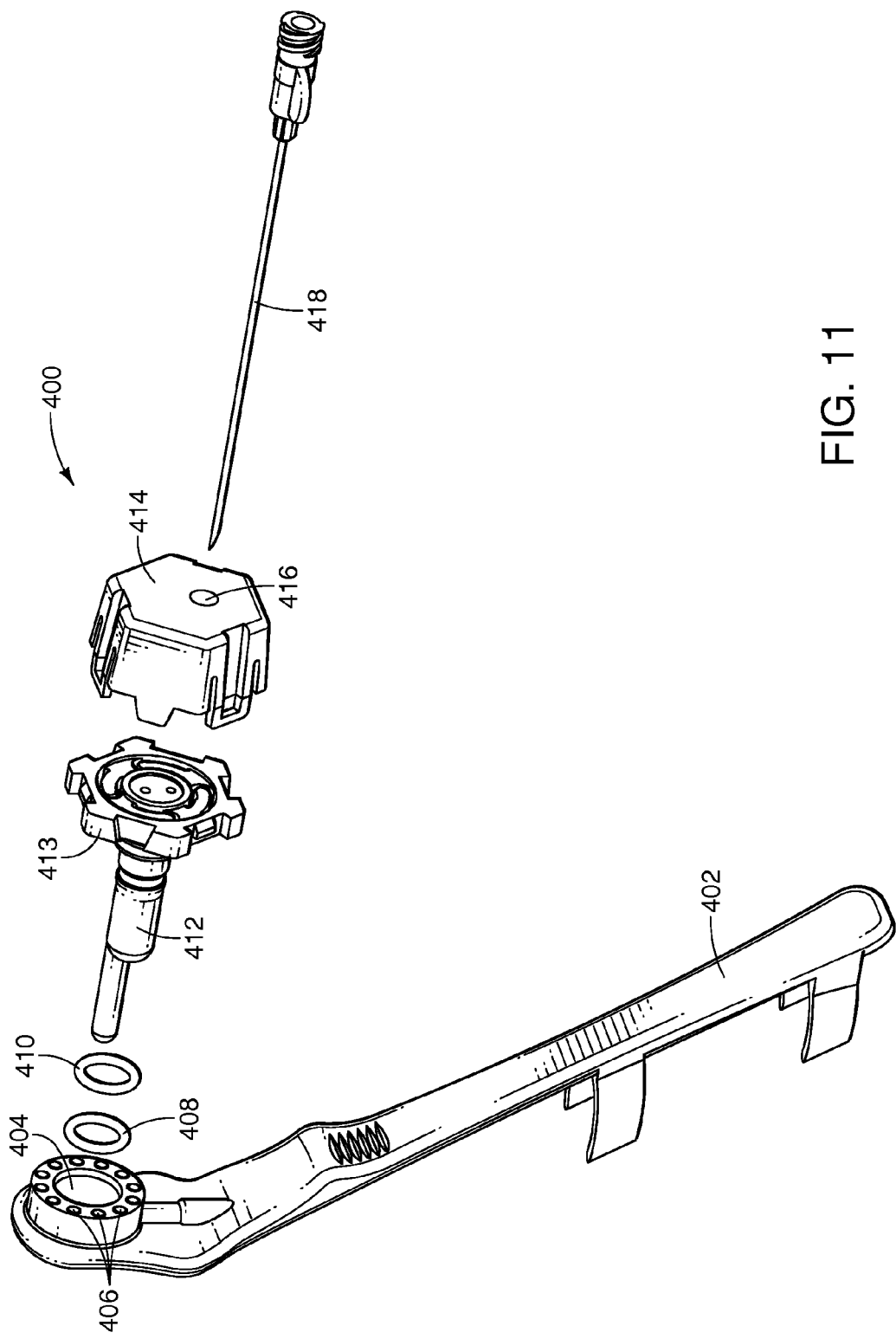
FIG. 11 is an exploded view of another urethral needle guide device similar in some respects to that of FIG. 1, but having a different rotatable body and needle guide cap.

FIG. 11 illustrates another embodiment of the invention in a needle guide device 400, shown in an exploded configuration. Device 400 is similar in many respects to the device illustrated in FIGS. 1-6, having a handle 402 with an aperture 404 surrounded by a series of engagement bumps 406. A rotatable body 412, rotation selection knob 413, O-rings 408 and 410, and a needle guide cap 414 are included in device 400. Needle guide cap 414 has a needle receiving aperture 416 for receiving a hypodermic needle 418.

Figure 12:
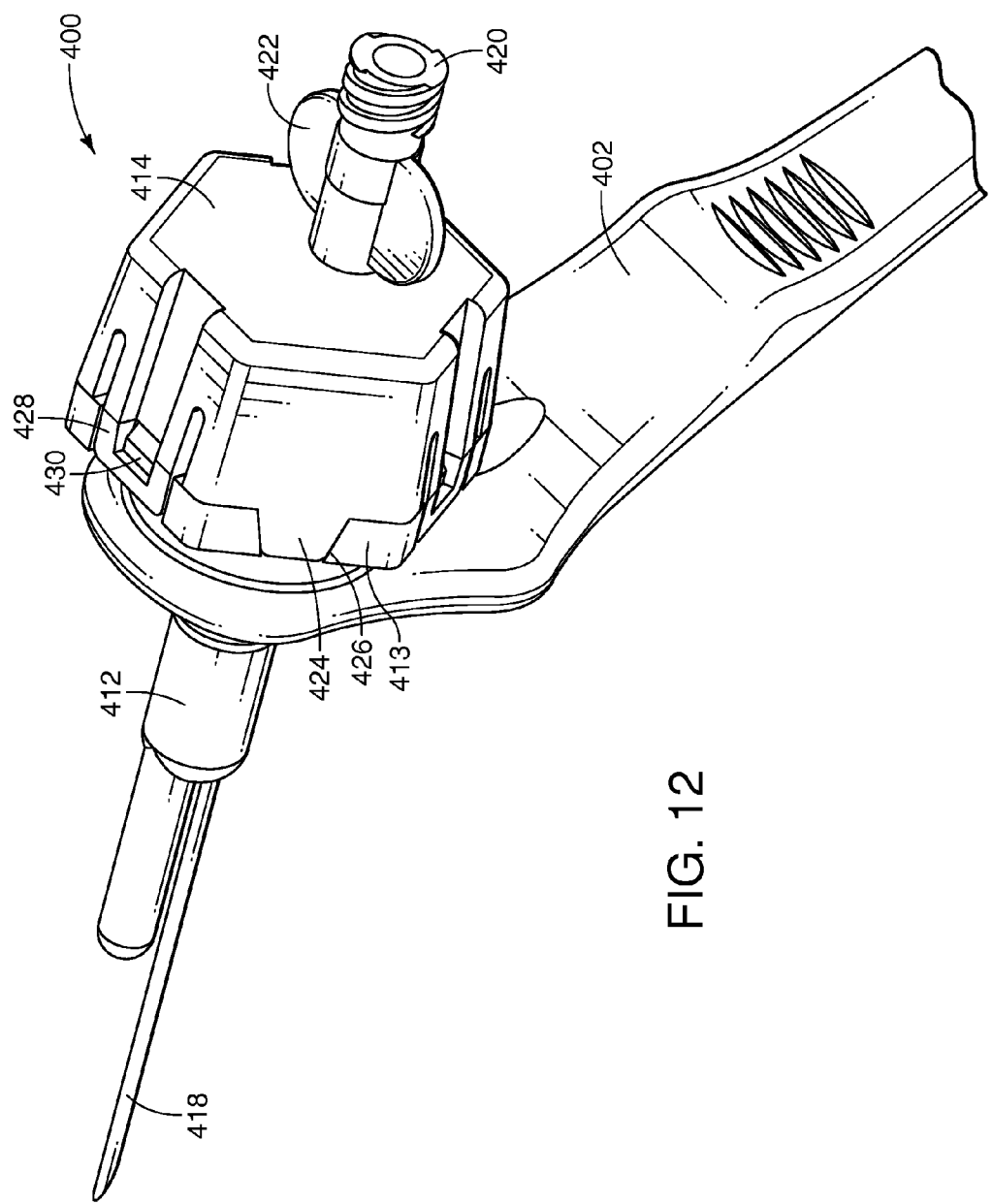
FIG. 12 is a fragmentary, perspective view of the device of FIG. 11, having the needle guide cap snapped in place over the rotatable body.

FIG. 12 illustrates device 400 in an assembled configuration, having handle 402, rotatable body 412, needle 418, and needle guide cap 414 as previously described. Needle 418 is secured to a proximal Luer fitting hub 420 having wings 422. Needle guide cap 414 has guide arms 424 fitting into matching guide recesses 426 which direct cap 414 into proper engagement with rotation selection knob 413. Cap 414 also has locking engagement arms 428 each snapping into place over an engagement tab 430 on rotation selection knob 413.

Figure 13:
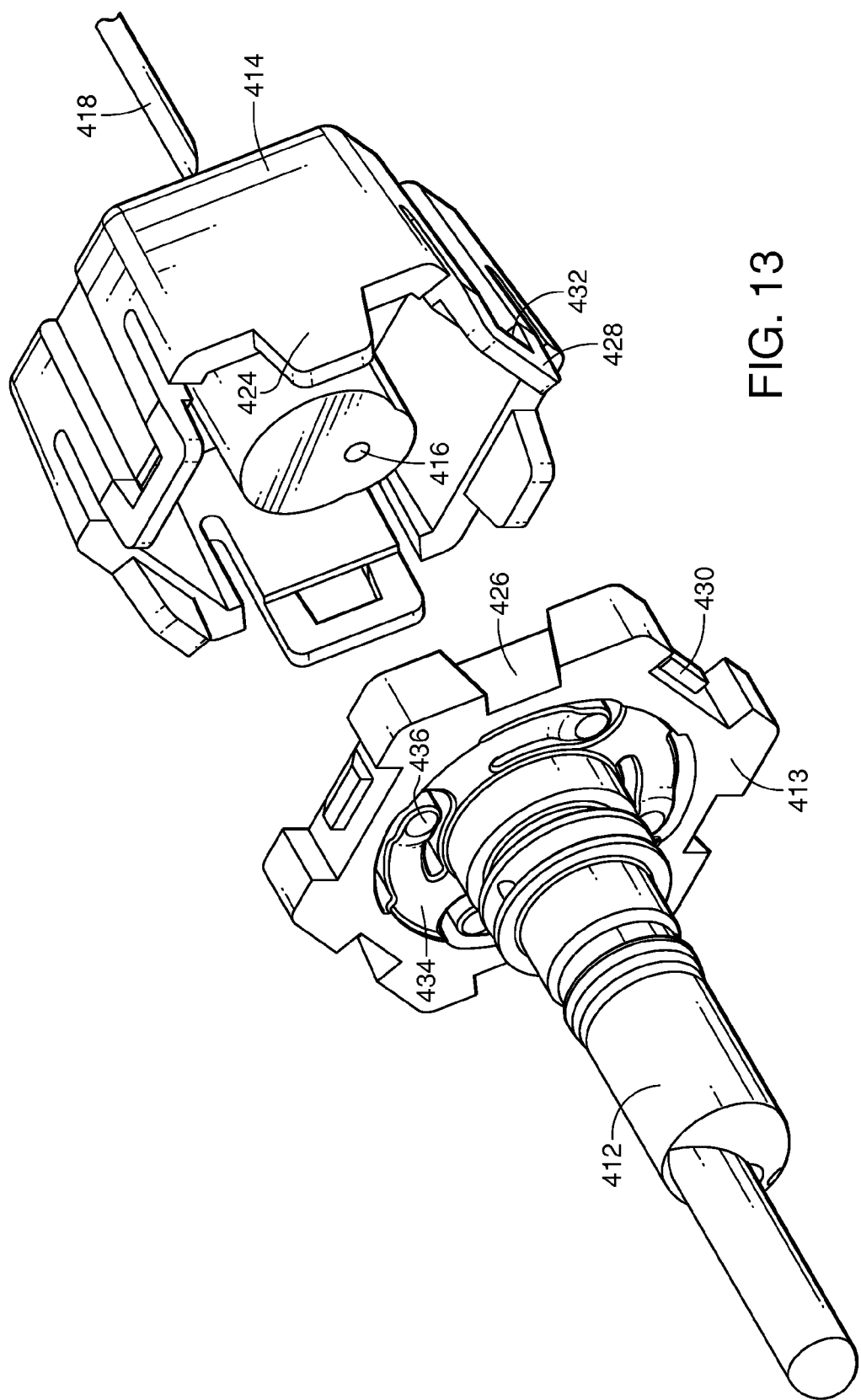
FIG. 13 is a fragmentary, perspective view of the rotatable body and cap of FIG. 11, shown from the front.

FIG. 13 illustrates rotatable body 412 and rotation selection knob 413 in more detail. Rotation selection knob 413 includes four arcuate latching engagement fingers 434 each having an engagement depression 436 for engaging bumps 406 shown in FIG. 11. The spring action of finger 434 allows holes 436 to be repeatedly forced up and over bumps 406, then settle into and engage the next bump as rotation selection knob 413 is rotated. Needle 418, needle receiving aperture 416, guide arm 424, guide recess 426, locking engagement arm 428, engagement aperture 432, and engagement tab 430 are as previously described.

Figure 14:
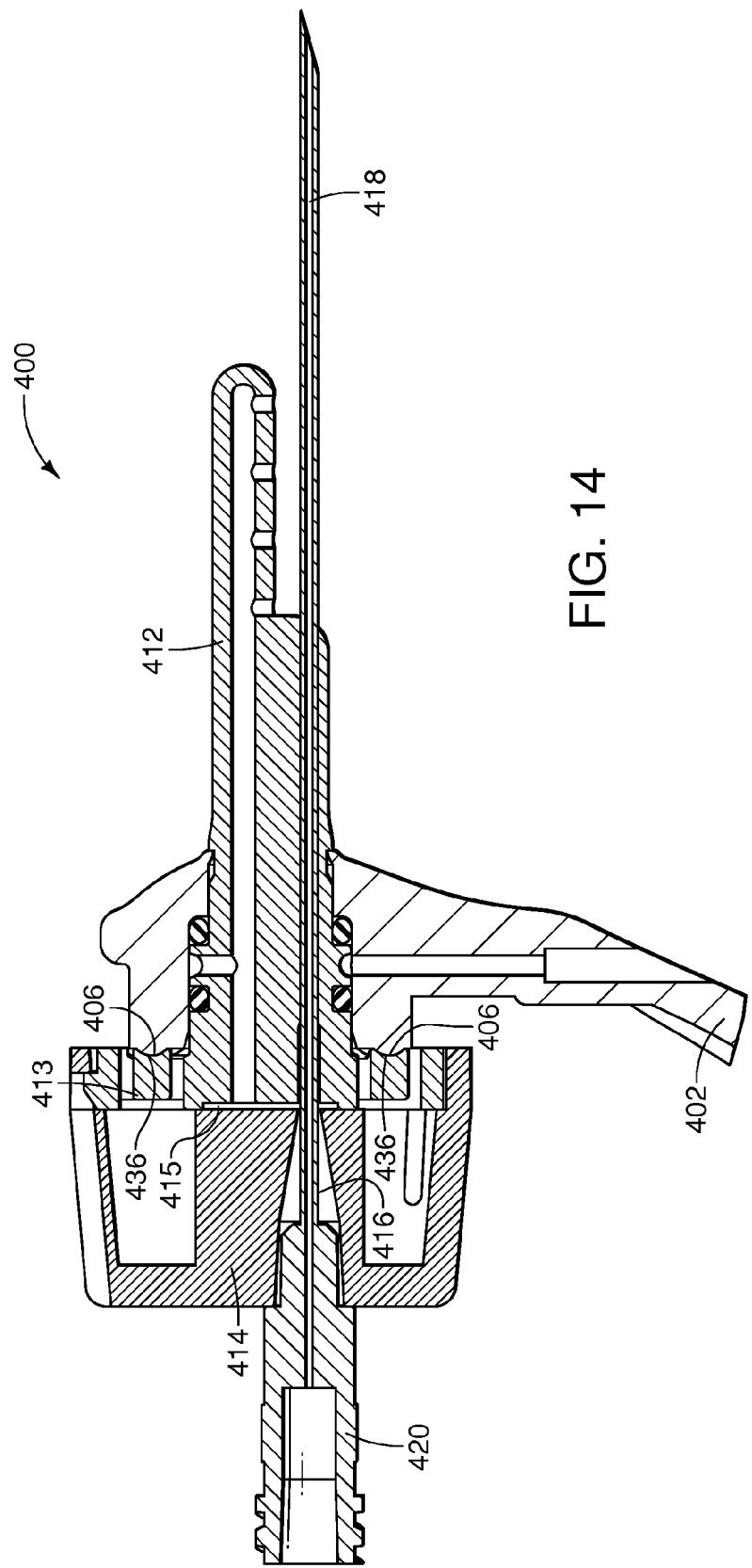
FIG. 14 is a fragmentary, cross-sectional view of the handle, rotatable body, needle guide cap, and needle of FIG. 11, with a septum disposed between the cap and rotatable body.

FIG. 14 illustrates device 400 in cross section. Needle 418 is inserted through needle aperture 416 in needle guide cap 414. Needle 418 punctures a polymeric septum 415 disposed between needle guide cap 414 and the proximal face of selection knob 413. Rotation selection knob 413 is assembled with depressions 436 engaged with bumps 406. Handle 402, rotatable body 412, and needle hub 420 are as previously described. In some embodiments, needle guide cap 414 has an elongate needle guide proximal portion, similar to that shown at 272 in FIG. 8. This elongate needle guide proximal portion can be sufficiently long to allow needle 418 to be withdrawn entirely into rotatable body 412. This allows needle 418 to rest hands free in the cap and proximal guide portion without the needle bending or breaking. This enables the treating physician to grip handle 402 with one hand while rotating the selection knob 413 with the other hand. Needle 418 is carried with rotating rotation selection knob 413 to the next injection position.

Referring again to FIG. 2, in use, elongate member 40 may be inserted into the female urethra. The urethral wall will likely be snugly fit about proximal portion 42 and may be somewhat distended by it. The urethral wall will distally pass over more distal portion 46. A vacuum can be induced by simply pulling on the barrel of the syringe, previously discussed. A vacuum will thus be generated through ports 60 and 62 disposed along elongate member 40. This will predictably pull the urethral wall to conform against elongate distal portion 46 and proximal portion 42. This places a region of the urethral wall directly and predictably in front of shoulder or transition region 44. This conformed tissue region can thus form a plane or curved surface which intersects a linear distal extension of the needle lumen, where the needle lumen is substantially parallel with the center axis of rotation of rotatable body 40. With the vacuum being applied to secure the tissue in place against the elongate body, the needle can be advanced to pierce the tissue surface and extend further into the tissue. The needle can be advanced along a path which lies at a relatively constant depth beneath the urethral wall, for a travel distance that can be two, three, or more multiples of the depth. Once the needle is in place, the vacuum may be released, and the bulking agent can be injected. As used herein, the phrase "bulking agent" can include beads, particles, polymers, pre-polymers, and so called muscle enhancers and constriction agents. In some methods, a liquid, for example saline or water, is injected through the device and into the urethra or bladder at a different point in the procedure, in addition to the bulking agent injected into the urethral wall.

A bulking agent syringe can be advanced through rotation selection knob 38 with the needle extending distally from needle distal port 64. As can be seen in FIG. 2, the distance of the needle penetration beneath the urethral wall will be substantially constant over the length of elongate member distal portion 46. Of course, at the point of entry, the needle may even approach a perpendicular angle of entry, but will run substantially parallel to the urethral wall once the penetration travel distance becomes greater.

The tissue bulking injection device needle can be advanced along substantially the entire length of elongate distal portion 46 without fear of injecting too deeply beneath the urethral wall, as the distance beneath the urethral wall is substantially constant over the length of elongate portion distal region 46. In some methods, the needle is advanced to the maximum distal extent, and the tissue bulking material is injected while the injecting needle is retracted proximally. Once sufficient material has been injected, rotation selection knob 38 can be rotated after the needle has been withdrawn within proximal portion 42. In one method, proximal portion 42 and rotation selection knob 38 are rotated about 120°, followed by pulling vacuum, following the distal advancement of the needle through needle aperture 64 into another portion of tissue. In some methods, the rotation selection knob is rotated to place the needle at the 2 O'clock, 6 O'clock, and 10 O'clock positions. This can be repeated until the entire urethral circumference has been sufficiently treated.

Some methods can utilize a device pressure sensor, previously described. The urethral wall pressure can be measured before beginning the procedure, and monitored during the bulking process. In some methods, the bulking is continued until the inward pressure of the urethral wall reaches a target level, whereupon the bulking is stopped.

In one embodiment, three positions of 2 O'clock, 6 O'clock, and 10 O'clock, about 120° apart, are selected and injected using the present device and methods. In some previous devices, a needle was used to inject the bulking material into the urethral wall to approach the wall at an angle with respect to the longitudinal central axis of the urethra. In these methods, the advancement of the injecting needle too far would inject undesirably deep beneath or through the urethral wall. FIG. 2 shows that as long as the urethral wall is conformed along distal portion 46, then the added insertion depth will be parallel to the urethral wall, not transverse or at an angle to it. This depth may be calculated and set in advance by varying the diameter of the rotatable body and the offset of the needle lumen along the shoulder or transition portion of the urethral needle guide device.

Various examples of devices and methods have been presented in order to illustrate, not limit the present invention. It is anticipated that various modifications will occur to those skilled in the art without departing from the spirit and scope of the invention as defined by the following claims.

The invention claimed is:

1. An apparatus for augmenting urethral tissue, the apparatus comprising:
a handle; and
an elongate member rotatably coupled to the handle so that the handle can be held in a stationary position as the elongate member is rotated with respect to the handle about a center of rotation, the elongate member having a channel for receiving a needle and a vacuum lumen for drawing a vacuum; the elongate member further having a distal portion extending distally from the handle, the distal portion having two regions, a proximal region and a distal region; wherein the proximal and distal regions each have generally rounded outer surfaces; wherein the distance around the generally rounded outer surface of the proximal region is greater than the distance around the generally rounded outer surface of the distal region; the proximal region extending to and ending at a shoulder region and the distal region extending beyond the shoulder region in a generally rounded columnar shape having a smooth generally rounded distal end such that the generally rounded outer surface of the distal region is smooth and generally without disruption with the exception of the at least one outwardly opening vacuum port; wherein the vacuum lumen extends through the proximal region and into the distal region where the vacuum lumen is in fluid communication with the at least one outwardly opening vacuum port disposed on the generally rounded outer surface of the distal region; wherein the proximal region ends at the shoulder region and the channel extends the length of the proximal region and communicates with and terminates at a distal aperture disposed in the shoulder region proximate the at least one vacuum port in the generally rounded outer surface of the distal region; wherein the distal region is generally cylindrical in shape along its entire length and rotates about the center of rotation when the elongate member is rotated; wherein the distal region extends beyond the distal aperture and has a generally uniform circumference and an even surface, which allows the urethral tissue to lie evenly along the generally rounded outer surface.

2. The apparatus of claim 1, wherein the distal region has a side wall, and in which at least one of the vacuum ports extends through the side wall of the distal region of the elongate member.

3. The apparatus of claim 1, wherein the handle has an upper portion and the elongate member is disposed substantially orthogonal to the upper portion of the handle.

4. The apparatus of claim 1, further comprising a vacuum generating device operably coupled to the handle for providing a vacuum to the vacuum lumen.

5. The apparatus of claim 4, in which the vacuum generating device includes a syringe operably coupled to the handle.

6. The apparatus of claim 5, in which the syringe is releasably coupled to the handle.

7. The apparatus of claim 5, in which the syringe is releasably coupled to the handle with at least two resilient members.

8. The apparatus of claim 5, wherein the syringe includes a plunger sealingly and slidably disposed within a barrel, wherein the barrel has an interior in fluid communication with the vacuum lumen, such that a vacuum can be generated by retracting the plunger within the barrel.

9. The apparatus of claim 5, further including a Luer fitting in communication with the vacuum lumen, wherein the syringe is in fluid communication with the vacuum lumen through the Luer fitting.

10. The apparatus of claim 1, wherein the apparatus includes cooperatively engaging elements coupled to the elongate member and the handle respectively, the cooperatively engaging elements being evenly spaced apart from each other to permit stable positioning of the elongate member on the handle when the elongate member is rotated to a position where the cooperatively engaging elements are engaged with each other.

11. The apparatus of claim 10, wherein the elongate member includes a proximal portion having a knob, in which at least some of the cooperatively engaging elements are disposed on the knob, the apparatus further comprising a cap cooperatively configured with the knob to be removably securable to the knob, the cap having a needle receiving aperture formed therethrough and located on the cap to be in line with the elongate member needle receiving channel when the cap is secured to the knob.

12. The apparatus of claim 1, wherein the elongate member is slidably coupled to the handle to allow longitudinal travel relative to the handle, and in which the elongate member and the handle are adapted to be cooperatively engaged to inhibit the travel.

13. The apparatus of claim 1, further comprising a remote viewing device disposed on the elongate member and an optical signal transmission line extending from the remote viewing device.

14. The apparatus of claim 1, further comprising a pressure sensor disposed on the elongate member and a pressure signal transmission line extending proximate to the pressure sensor.

* * * * *